United States Patent
Aizawa et al.

(10) Patent No.: US 9,902,697 B2
(45) Date of Patent: Feb. 27, 2018

(54) METHOD FOR PRODUCING 2-AMINO-6-METHYLNICOTINIC ACID

(71) Applicant: AGRO-KANESHO CO., LTD., Minato-ku (JP)

(72) Inventors: Ryo Aizawa, Tokorozawa (JP); Koichi Araki, Ushiku (JP)

(73) Assignee: AGRO-KANESHO CO., LTD., Minato-ku (JP)

(*) Notice: Subject to any disclaimer, the term of this patent is extended or adjusted under 35 U.S.C. 154(b) by 0 days.

(21) Appl. No.: 15/317,255

(22) PCT Filed: Jun. 27, 2014

(86) PCT No.: PCT/JP2014/067260
§ 371 (c)(1),
(2) Date: Dec. 8, 2016

(87) PCT Pub. No.: WO2015/198486
PCT Pub. Date: Dec. 30, 2015

(65) Prior Publication Data
US 2017/0129858 A1    May 11, 2017

(51) Int. Cl.
*C07D 213/803*    (2006.01)

(52) U.S. Cl.
CPC .............. *C07D 213/803* (2013.01)

(58) Field of Classification Search
None
See application file for complete search history.

(56) References Cited

U.S. PATENT DOCUMENTS

| | | |
|---|---|---|
| 4,327,219 A | 4/1982 | Gelbein |
| 4,963,561 A | 10/1990 | Lesher et al. |
| 2007/0105943 A1 | 5/2007 | Nakamoto et al. |
| 2007/0197558 A1 | 8/2007 | Betebenner et al. |
| 2007/0232627 A1 | 10/2007 | Betebenner et al. |
| 2007/0232645 A1 | 10/2007 | Rockway et al. |
| 2009/0227799 A1 | 9/2009 | Nakamoto et al. |
| 2010/0256139 A1 | 10/2010 | Rockway et al. |
| 2011/0009454 A1 | 1/2011 | Matsuzaki et al. |
| 2011/0160233 A1 | 6/2011 | Betebenner et al. |
| 2011/0195999 A1 | 8/2011 | Nakamoto et al. |
| 2012/0022262 A1 | 1/2012 | Ott et al. |
| 2015/0175551 A1 | 6/2015 | Aizawa et al. |

FOREIGN PATENT DOCUMENTS

| | | |
|---|---|---|
| CN | 101812016 A | 8/2010 |
| JP | 56-166174 A | 12/1981 |
| JP | 2010-83861 A | 4/2010 |
| JP | 2010-524877 A | 7/2010 |
| WO | 2005/033079 A1 | 4/2005 |
| WO | 2007/076034 A2 | 7/2007 |
| WO | 2014/006945 A1 | 1/2014 |

OTHER PUBLICATIONS

International Search Report issued Jul. 22, 2014, in PCT/JP2014/067260, filed Jun. 27, 2014.
Office Action mailed Jun. 3, 2016, in Taiwanese Patent Application No. 104113086 (4 pages).
Zawisza et al., "Synthesis and properties of the new derivatives of 3H-pyrido-[3,2-e]-1,3-thiazin-4-one", Acta Poloniae Pharmaceutica, vol. 38, No. 2, 1981, p. 145-152.
Thomas et al., "Synthesis, in vitro and in vivo activity of thiamine antagonist transketolase inhibitors", Bioorganic & Medicinal Chemistry Letters, vol. 18, 2008, p. 2206-2210.
Taylor, et al., "Pyridine-1-oxides. I. Synthesis of some nicotinic acid derivatives", Journal of Organic Chemistry, vol. 19, 1954, p. 1633-1640.
Notice of Reasons for Rejection, in JP Patent Application No. 2016-528966, dated Jul. 10, 2017 with English Translation.
Gian Paolo Vailerini, et al., "Journal of Medicinal Chemistry, 2-Aminonicotinic acid 1-oxides are chemically stable inhibitors of quinolinic acid synthesis in the mammalian brain: a step toward new antiexcitotoxic agents" 2013, vol. 56, pp. 9482-9495.

*Primary Examiner* — Zinna Northington Davis
(74) *Attorney, Agent, or Firm* — Oblon, McClelland, Maier & Neustadt, L.L.P.

(57) ABSTRACT

The present invention provides a method for producing 2-amino-6-methylnicotinic acid represented by formula [I], wherein the production method comprises: (a) reacting 2-chloro-3-cyano-6-methylpyridine represented by formula [II] in an ammonia aqueous solution to obtain a reaction solution containing 2-amino-6-methylnicotinamide represented by formula [III]; and (b) removing the ammonia from the reaction solution, then reacting the 2-amino-6-methylnicotinamide represented by formula [III] with a base to produce 2-amino-6-methylnicotinic acid represented by formula [I].

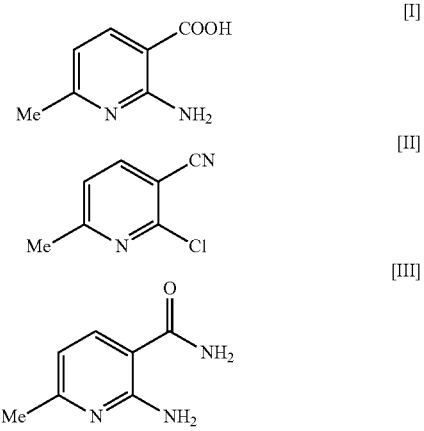

2 Claims, No Drawings

METHOD FOR PRODUCING 2-AMINO-6-METHYLNICOTINIC ACID

TECHNICAL FIELD

The present invention relates to a method for producing 2-amino-6-methylnicotinic acid. Specifically, the present invention relates to a method for producing 2-amino-6-methylnicotinic acid at a high yield with high purity, the 2-amino-6-methylnicotinic acid being a production intermediate compound for a compound useful as an active ingredient of a pharmaceutical or agricultural chemical.

BACKGROUND ART

Pharmaceuticals or agricultural chemicals produced by using 2-amino-6-methylnicotinic acid as an intermediate have been described, for example, in International Publication No. WO2005/33079, Japanese Patent Application Publication No. 2010-083861, and International Publication No. WO2014/6945.

As a method for producing 2-amino-6-methylnicotinic acid, there are known methods such as a method including hydrolyzing 2-chloro-3-cyano-6-methylpyridine under an acidic condition or a basic condition and reacting the obtained 2-chloro-6-methylnicotinic acid with ammonia, and a method including reacting 2-chloro-3-cyano-6-methylpyridine with ammonia in an organic solvent such as alcohol to obtain 2-amino-3-cyano-6-methylpyridine, followed by hydrolyzing the 2-amino-3-cyano-6-methylpyridine under an acidic condition or a basic condition. These methods are described, for example, in Japanese Patent Application Publication No. 2010-083861, Chinese Patent Application Publication No. 101812016, International Publication No. WO2007/76034, Bioorganic and Medicinal Chemistry Letters, Vol. 18 (6), p. 2206 (2008), and Acta Poloniae Pharmaceutica, Vol. 38 (2), p. 145 (1981).

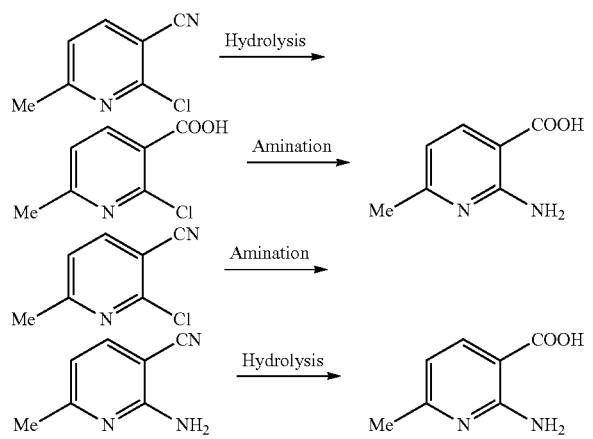

In the conventional production methods, a purification operation is inevitable for the reason that an unreacted ingredient remains or other reasons. In addition, the conventional production methods cannot control a by-product of the reaction, and therefore is a method for producing the target product at a low yield. Specifically, when 2-chloro-6-methylnicotinic acid reacts with an aqueous solution of ammonia, 2-hydroxy-6-methylnicotinic acid is produced as a by-product at about 15 to 20 %. For this reason, it is difficult to improve the yield of 2-amino-6-methylnicotinic acid. Meanwhile, the amination reaction of 2-chloro-3-cyano-6-methylpyridine using an organic solvent such as alcohol cannot be completed even by using a saturated ammonia solution, and therefore requires a removal of the solvent and purification by column chromatography or the like. Hence, any of the conventional production methods is not exactly an easy production method capable of obtaining a target product at a high yield with high purity. Therefore, there is a demand for the development of an easy industrial production method capable of obtaining a target product at a high yield with high purity.

The present inventors have earnestly studied to solve the aforementioned problem, and consequently have arrived at the present invention by finding that 2-amino-6-methylnicotinic acid with high purity can be obtained at high yield by: reacting 2-chloro-3-cyano-6-methylpyridine in an aqueous solution of ammonia to obtain 2-amino-6-methylnicotinamide; removing the ammonia from the reaction solution by pressure reduction or the like; and thereafter adding a base such as alkali metal hydroxide to the resultant solution to react the 2-amino-6-methylnicotinamide with the base.

Specifically, an embodiment of the present invention provides a method for producing 2-amino-6-methylnicotinic acid represented by the following formula [I]:

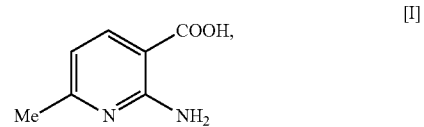 [SMILES: Cc1ccc(C(=O)O)c(N)n1]

the method comprising:

(a) reacting 2-chloro-3-cyano-6-methylpyridine represented by the following formula [I]:

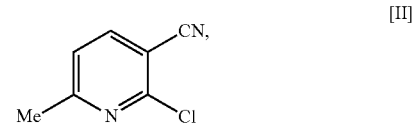

in an aqueous solution of ammonia to obtain a reaction solution containing 2-amino-6-methylnicotinamide represented by the following formula [III]:

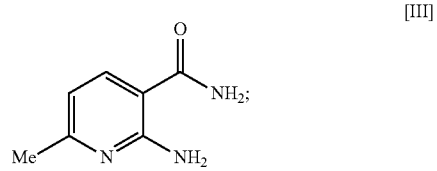 [SMILES: Cc1ccc(C(N)=O)c(N)n1]

and (b) removing the ammonia from the reaction solution, subsequently reacting the 2-amino-6-methylnicotinamide represented by the formula [III] with a base to produce the 2-amino-6-methylnicotinic acid represented by the formula [I].

In the embodiment of the present invention, the 2-amino-6-methylnicotinic acid represented by the formula [I] is produced by a one-pot synthesis from the 2-chloro-3-cyano-6-methylpyridine represented by the formula [II].

DESCRIPTION OF EMBODIMENTS

Hereinafter, the present invention is described in detail.

In an embodiment of a production method of the present invention, an aqueous solution of ammonia at 5 to 30%, preferably an aqueous solution of ammonia at 20 to 30% is added to a compound of the formula [II] in an amount of 2 to 100 times, preferably 10 to 50 times the molar amount of the compound of the formula [II], followed by stirring at 0 to 200° C. for 5 minutes to 10 hours, preferably at 120 to 180° C. for 2 to 10 hours. Thereafter, the ammonia in the reaction solution containing a compound of the formula [III] is removed by pressure reduction or the like, and a base such as sodium hydroxide or potassium hydroxide is added, in an amount of 1 to 10 times, preferably 1 to 4 times the molar amount of the compound of the formula [III],to the reaction solution containing the compound of the formula [III], followed by stirring at 0 to 100° C. for 5 minutes to 5 hours, preferably at 80 to 100° C. for 2 to 5 hours. After the reaction, in order to obtain the compound of the formula [I], an acid such as hydrochloric acid is added to the reaction solution to neutralize the reaction solution, and precipitated crystals are filtered out. The crystals filtered out are washed by water, and then are dried. Thereby, the compound of the formula [I] which is the target compound can be obtained very easily at a high yield with high purity.

In an embodiment of the production method of the present invention, an aqueous solution of ammonia at 5 to 30%, preferably an aqueous solution of ammonia at 20 to 30% is added to the compound of the formula [II].

In an embodiment of the production method of the present invention, the aqueous solution of ammonia is used in an amount of 2 to 100 times, preferably 10 to 50 times the molar amount of the compound of the formula [II].

In an embodiment of the production method of the present invention, a reaction of the compound of the formula [II] with the aqueous solution of ammonia is carried out with stirring at 0 to 200° C. for 5 minutes to 10 hours, preferably at 120 to 180° C. for 2 to 10 hours.

In an embodiment of the production method of the present invention, the ammonia in the reaction solution containing the compound of the formula [III] is removed by an operation such as pressure reduction.

In an embodiment of the production method of the present invention, the reaction of the compound of the formula [III] with the base is caused by adding the base in an amount of 1 to 10 times, preferably 1 to 4 times the molar amount of the compound of the formula [III], to the reaction solution which contains the compound of the formula [III] and from which the ammonia has been removed.

In an embodiment of the production method of the present invention, the reaction of the compound of the formula [III] with the base is carried out with stirring at 0 to 100° C. for 5 minutes to 5 hours, preferably at 80 to 100° C. for 2 to 5 hours.

In an embodiment of the production method of the present invention, after the reaction of the compound of the formula [III] with the base, an acid such as hydrochloric acid is added to the reaction solution to neutralize the reaction solution, and precipitated crystals are filtered out in order to obtain the compound of the formula [I]. Then, the crystals filtered out are washed by water and then are dried, so that the compound of the formula [I] which is the target compound can be obtained.

In the production method of the present invention, a base usable in the reaction of the compound of the formula [III] with the base is, for example, an alkali metal hydroxide such as lithium hydroxide, sodium hydroxide or potassium hydroxide, for example, an alkali metal carbonate such as sodium carbonate, potassium carbonate, or cesium carbonate, for example, an alkali earth metal hydroxide such as magnesium hydroxide or calcium hydroxide, or for example, an alkali earth metal carbonate such as magnesium carbonate or calcium carbonate. The preferable base is lithium hydroxide, sodium hydroxide, or potassium hydroxide.

The 2-chloro-3-cyano-6-methylpyridine used in the production method of the present invention and represented by the formula [II] may be one commercially available, or may be synthesized directly from a publicly known compound in accordance with, for example, the method described in Heterocycles, Vol. 41 (6), p. 1307 (1995).

The compound of the formula [I] produced by the production method of the present invention is useful as a production intermediate compound for a compound useful as an active ingredient of a pharmaceutical or agricultural chemical.

In an embodiment of the production method of the present invention, the compound of the formula [II] is reacted in an aqueous solution of ammonia to obtain the reaction solution containing the compound of the formula [III], thereafter the ammonia is removed from the aforementioned reaction solution, subsequently the compound represented by the formula [III] is reacted with a base without isolating it, and thereby the target compound represented by the formula [I] can be produced. In other words, in the embodiment of the production method of the present invention, the target compound represented by the formula [I] is produced by one-pot synthesis including: obtaining the reaction solution containing the compound of the formula [III] by reacting the compound of the formula [II] in the aqueous solution of ammonia; removing the ammonia from the aforementioned reaction solution; and reacting the compound represented by the formula [III] with the base.

EXAMPLES

Hereinafter, the present invention is further described using Examples, but the scope of the present invention is not limited at all to these Examples.

Example 1

Synthesis of 2-Amino-6-Methylnicotinic Acid

An aqueous solution of ammonia at 28% (70 mL) was added to 2-chloro-3-cyano-6-methylpyridine (6.10 g), followed by reaction in an autoclave at 170° C. for 7 hours. The reaction solution was cooled to a room temperature, and the ammonia was removed under reduced pressure. Potassium hydroxide (9.00 g) was added to the reaction solution from which the ammonia had been removed, followed by heating and stirring at 100° C. for 3 hours. The reaction solution was cooled to a room temperature, and was prepared at pH 4 to 5 by dropwise addition of 4N hydrochloric acid. The precipitated crystals were filtered out, and then were further washed by water and dried by air. In this way, 5.04 g of 2-amino-6-methylnicotinic acid was obtained (yield: 82.9%). The purity analysis by a liquid chromatography was conducted, and the purity was found to be 97.06%, which is high purity.

$^1$H-NMR (DMSO-d6) δppm: 2.28 (3H, s), 6.44 (1H, d), 6.82-7.44 (2H. br), 7.92 (1H, d)

Comparative Example 1

75 % sulfuric acid (10 mL) was added to 2-chloro-3-cyano-6-methylpyridine (3.05 g), followed by heating and stirring at 100° C. for 2 hours. The reaction solution was cooled to a room temperature, and was poured little by little to ice water. The ice water was stirred for 10 minutes and the precipitated crystals were filtered out and dried. In this way, 2.91 g of 2-chloro-6-methylnicotinic acid was obtained (85%). An aqueous solution of ammonia at 28% (35 mL) was added to the obtained 2-chloro-6-methylnicotinic acid (2.91 g), followed by reaction in an autoclave at 170° C. for 40 hours. The reaction solution was cooled to a room temperature and the ammonia was removed under reduced pressure. The precipitated crystals were filtered out, and then were further washed by water and dried by air. Thus, 1.91 g of 2-amino-6-methylnicotinic acid was obtained (yield 74%). The total yield was 62.9%.

Comparative Example 2

An ammonia gas was injected to ethanol (50 mL) to prepare an ethanol solution of saturated ammonia (about 10%). Then, 2-chloro-3-cyano-6-methylpyridine (3.05 g) was added to the ethanol solution, followed by reaction in an autoclave at 170° C. for 15 hours. The reaction solution was cooled to a room temperature, and was condensed under reduced pressure. Water was added to the residue, and the residue was extracted with ethyl acetate, and was dried and condensed with anhydrous sodium sulfate. The obtained residue was purified by silica gel column chromatography (a gradient of hexane:ethyl acetate is set to 9:1 to 1:9) to obtain 1.10 g of 2-amino-3-cyano-6-methylpyridine (41%). 15% potassium hydroxide (10 mL) was added to the 1.10 g of 2-amino-3-cyano-6-methylpyridine thus obtained, followed by heating and stirring at 100° C. for 3 hours. The reaction solution was cooled to a room temperature, and was prepared at pH 4 to 5 by dropwise addition of 4N hydrochloric acid. The precipitated crystals were filtered out and then were further washed by water and dried by air. Thus, 1.18 g of 2-amino-6-methylnicotinic acid was obtained (yield: 94%). The total yield was 38.5%.

As described above, the production method of the present invention is a method for producing 2-amino-6-methylnicotinic acid at a high yield with high purity, the 2-amino-6-methylnicotinic acid being a production intermediate compound for a compound useful as an active ingredient of a pharmaceutical or agricultural chemical.

The invention claimed is:
1. A method for producing 2-amino-6-methylnicotinic acid represented by the following formula [I]:

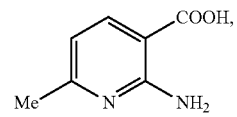

the method comprising:
(a) reacting 2-chloro-3-cyano-6-methylpyridine represented by the following formula [II]:

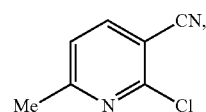

in an aqueous solution of ammonia to obtain a reaction solution containing 2-amino-6-methylnicotinamide represented by the following formula [III]:

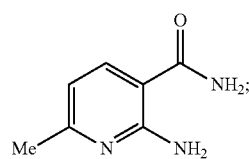

and
(b) removing the ammonia from the reaction solution, and subsequently reacting the 2-amino-6-methylnicotinamide represented by the formula [III] with a base to produce the 2-amino-6-methylnicotinic acid represented by the formula [I].
2. The method for producing 2-amino-6-methyinicotinic acid according to claim 1, wherein the 2-amino-6-methylnicotinic acid represented by the formula [I] is produced by one-pot synthesis from the 2-chloro-3-cyano-6-methylpyridine represented by the formula [II].

* * * * *